United States Patent
Li et al.

(10) Patent No.: US 12,152,059 B2
(45) Date of Patent: Nov. 26, 2024

(54) METHOD OF TREATING NASH USING A LONG-ACTING MUTANT HUMAN FIBROBLAST GROWTH FACTOR

(71) Applicant: TASLY BIOPHARMACEUTICALS CO., LTD., Shanghai (CN)

(72) Inventors: Jian Li, Tianjin (CN); Jun Han, Tianjin (CN); Xiaohui Ma, Tianjin (CN); Ping Tai, Tianjin (CN); Genbei Wang, Tianjin (CN); Xiaodan Cao, Tianjin (CN); Ruijing Huang, Tianjin (CN); Yongjie Jin, Tianjin (CN); Jing Li, Tianjin (CN); Chen Chen, Tianjin (CN); Guoyong Jia, Tianjin (CN); Yuanyuan Wang, Tianjin (CN)

(73) Assignee: TASLY BIOPHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/520,053

(22) Filed: Jul. 23, 2019

(65) Prior Publication Data
US 2019/0367574 A1    Dec. 5, 2019

Related U.S. Application Data

(63) Continuation-in-part of application No. PCT/CN2018/079482, filed on Mar. 19, 2018.

(30) Foreign Application Priority Data

Mar. 22, 2017    (CN) .................... 201710172824.0

(51) Int. Cl.
| | |
|---|---|
| C07K 14/50 | (2006.01) |
| A61K 38/00 | (2006.01) |
| A61K 38/18 | (2006.01) |
| A61P 1/16 | (2006.01) |

(52) U.S. Cl.
CPC ............... *C07K 14/50* (2013.01); *A61P 1/16* (2018.01); *A61K 38/00* (2013.01); *A61K 38/1825* (2013.01)

(58) Field of Classification Search
None
See application file for complete search history.

(56) References Cited

U.S. PATENT DOCUMENTS

| | | | | |
|---|---|---|---|---|
| 6,716,626 | B1 * | 4/2004 | Itoh ................. | C07K 14/50 435/254.2 |
| 10,286,078 | B2 * | 5/2019 | Shen ................. | A61K 47/554 |
| 2013/0190232 | A1 | 7/2013 | Tagmose et al. | |
| 2013/0252884 | A1 * | 9/2013 | Garibay ............. | A61K 38/1825 514/4.8 |
| 2016/0115213 | A1 * | 4/2016 | Morin ................ | A61P 1/00 514/4.8 |
| 2016/0168223 | A1 | 6/2016 | Belouski et al. | |
| 2016/0287713 | A1 * | 10/2016 | Shen ................. | A61P 9/00 |

FOREIGN PATENT DOCUMENTS

| | | | |
|---|---|---|---|
| CN | 101935346 A | * | 1/2011 |
| CN | 103124562 A | | 5/2013 |
| CN | 103193878 A | | 7/2013 |
| CN | 103415300 A | | 11/2013 |
| CN | 103923207 A | * | 7/2014 |
| CN | 105792851 A | | 7/2016 |
| EP | 3603660 | * | 2/2020 |
| JP | 6069198 B2 | | 2/2017 |
| WO | WO 2005/091944 A2 | | 10/2005 |
| WO | WO 2015/038938 A1 | | 3/2015 |

OTHER PUBLICATIONS

Machine translation of CN101935346A, generated Aug. 6, 2020.*
Machine translation of CN103923207B generated Aug. 6, 2020.*
Machine translation of CN103193878A, generated Aug. 6, 2020.*
Xu et al., Diabetes, 58(1):250-9, 2009.*
Fisher et al., Gastroenterology 147(5):1073-1083, 2014.*
Kharitonenkov A, Beals JM, Micanovic R, Strifler BA, Rathnachalam R, et al. (2013) Rational Design of a Fibroblast Growth Factor 21-Based Clinical Candidate, LY2405319. PLoS One 8(3): e58575. doi: 10.1371/journal.pone.0058575.*
Ye et al., Yao Xue Xue Bao, Jul. 2012;47(7):897-903 (translated English abstract only).*
Brunt et al., Hepatology, 53 (3):810-820, 2011.*
Kleiner et al., Hepatology, 41(5):1313-1321, 2005.*
Chalasani et al., Gastroenterology, 142:1592-1609, 2012.*
International Patent Application No. PCT/CN2018/079482; Int'l Search Report; dated Jun. 27, 2018; 2 pages.
Zhu et al.; "FGF21 ameliorates nonalcoholic fatty liver disease by inducing autophagy"; Molecular and Cellular Biochemistry; vol. 420; 2016; p. 107-119.
European Patent Application No. 18771156.9; Extended Search Report; dated Dec. 3, 2020; 9 pages.
Gaich et al.; "The Effects of LY2405319, an FGF21 Analog, in Obese Human Subjects with Type 2 Diabetes"; *Cell Metabolism*; vol. 18; Sep. 2013; p. 333-340.

* cited by examiner

*Primary Examiner* — Marianne P Allen
(74) *Attorney, Agent, or Firm* — JONES DAY

(57) ABSTRACT

The invention relates to a method of treatment comprising administering a long-acting mutant human fibroblast growth factor to a subject in need thereof. The said long-acting mutant human fibroblast growth factor is mPEG-CH$_2$—N$^\alpha$H-mFGF21, wherein mFGF21 consists of SEQ ID NO: 1, and the said new use consists of a method of treating non-alcoholic steatohepatitis.

8 Claims, No Drawings
Specification includes a Sequence Listing.

METHOD OF TREATING NASH USING A LONG-ACTING MUTANT HUMAN FIBROBLAST GROWTH FACTOR

EARLIER FILED APPLICATIONS

The present application is a continuation in part of PCT/CN2018/079482, filed Mar. 19, 2018, which claims priority to CN201710172824.0, filed Mar. 22, 2017, which are herein incorporated by reference in their entirety.

SEQUENCE LISTING

The instant application contains a Sequence Listing which has been filed electronically in ASCII format and is hereby incorporated by reference in its entirety. Said ASCII copy, created on Jun. 1, 2021, is named 107244_000018_SL.txt and is 2,093 bytes in size.

TECHNICAL FIELD OF THE INVENTION

The present invention relates to the field of biomedicine, and particularly relates to the use of a long-acting mutant human fibroblast growth factor-21 in in a method of treating non-alcoholic steatohepatitis.

BACKGROUND ART

Non-alcoholic fatty liver disease (NAFLD), also known as non-alcoholic fatty liver, is caused by a variety of reasons. Lesions of this disease mainly occur in the hepatic lobule characterized by steatosis of hepatic parenchymal cells and triglyceride (TG) accumulation (fat content in liver tissues accounting for over 5% of liver wet weight or more than ⅓ hepatic cells presenting steatosis confirmed by histology). NAFLD is similar to alcoholic liver disease (ALD) in terms of pathological changes except absence of history of excessive drinking (equivalent to ethanol consumption, male <140 g/week, female <70 g/week) and other clinical pathological syndromes caused by specific liver-damaging factors. NAFLD and NASH have become the leading causes of liver disease in Western countries in the past 20 years. Without timely control, NAFLD can easily progress to NASH as fat continues to accumulate excessively. In addition to excessive accumulation of fat, NASH differs from NAFLD in the presence of inflammatory cell infiltration in liver, the degree of hepatic fibrosis, and the degree of liver cell damage. Furthermore, if NASH continues to progress without effective control, it is highly likely to cause hepatic fibrosis, cirrhosis and even liver cancer.

At present, there are no such drugs for NASH that can be clinically used for long term, safe and effective.

Fibroblast growth factor-21 (FGF-21) is another metabolic regulator recently discovered in vivo. It belongs to FGF family and specifically acts on liver, fat, and islet cells. FGF-21 can effectively and safely regulate blood glucose and blood fat independently of insulin, which has got researchers' a lot of attention. It has also been reported that FGF-21 can effectively prevent and treat NAFLD induced in vitro (Liu Min et al., Effect of fibroblast growth factor-21 on lipid metabolism of non-alcoholic fatty liver cell model induced in vitro. Journal of Jilin University, May 2012, Vol. 38, No. 3, 477-481.)

CN103193878A, hereby incorporated by reference in its entirety, discloses a new long-acting mutant human FGF and the polyethylene glycol (PEG) conjugate thereof. The protein structure of the said FGF-PEG conjugate consists of an amino acid sequence as follows.

Ala Tyr Pro Ile Pro Asp Ser Ser Pro Leu Leu Gln Phe Gly
Gly Gln Val Arg Gln Arg Tyr Leu Tyr Thr Asp Asp Ala
Gln Gln Thr Glu Ala His Leu Glu Ile Arg Glu Asp Gly
Thr Val Gly Gly Ala Ala Asp Gln Ser Pro Glu Ser Leu
Leu Gln Leu Lys Ala Leu Lys Pro Gly Val Ile Gln Ile
Leu Gly Val Lys Thr Ser Arg Phe Leu Cys Gln Arg Pro
Asp Gly Ala Leu Tyr Gly Ser Leu His Phe Asp Pro Glu
Ala Cys Ser Phe Arg Glu Leu Leu Leu Glu Asp Gly Tyr
Asn Val Tyr Gln Ser Glu Ala His Gly Leu Pro Leu Arg
Leu Pro Gln Lys Asp Ser Pro Asn Gln Asp Ala Thr Ser
Trp Gly Pro Val Arg Phe Leu Pro Met Pro Gly Leu Leu
His Glu Pro Gln Asp Gln Ala Gly Phe Leu Pro Pro Glu
Pro Pro Asp Val Gly Ser Ser Asp Pro Leu Ser Met Val
Gly Pro Ser Gln Gly Arg Ser Pro Ser Tyr Thr Ser (SEQ ID NO:1) Its preparation method is shown in Embodiment 4. This conjugate was later named by its inventors as FG (PEGylation Recombinant Human-mouse Chimeric Fibroblast Growth Factor 21 or mPEG-CH$_2$—N$^\alpha$H-mFGF21).

FG has the functions of regulating blood glucose, lowering blood triglycerides, and regulating total cholesterol et al. However, there have been no reports of FG in the treatment of NASH so far.

DESCRIPTION OF THE INVENTION

Disclosed herein the use of a long-acting mutant human FGF in the preparation of drugs for treating NASH.

As used herein, the long-acting mutant human FGF refers to mPEG-CH$_2$—N$^\alpha$H-mFGF21 (FG) or a salt.

As used herein, the use includes that FG or its salt can lower the levels of alanine aminotransferase (ALT) and aspartate aminotransferase (AST) in serum, improve steatosis and lobular inflammation, reduce the degree of hepatocellular ballooning degeneration, and improve liver damage.

As used herein, the NASH includes, not limited to, hepatitis-induced NASH, obesity-induced NASH, diabetes-induced NASH, insulin resistance-induced NASH, hypertriglyceridemia-induced NASH, abetalipoproteinemia-induced NASH, NASH induced by glycogen storage disease, NASH induced by Wake's Disease, NASH induced by Wolman's disease, and lipodystrophia-induced NASH.

As used herein, the drugs mean pharmaceutical compositions containing FG or a pharmaceutically acceptable salt thereof as the active pharmaceutical ingredient. The pharmaceutical compositions can be prepared into any pharmaceutically acceptable dosage form, including tablets, capsules, granules, pills, powders, paste, sublimed preparation, dustpowders, solutions, injections, suppositories, sprays, drops, patches, and drop pills. Drugs of the present invention are preferably prepared into injectable drugs, such as powder injections or liquid injections. The liquid injections include water injections, organic solvent injections, and suspension injections, et al.

The preparations of the pharmaceutical compositions for oral administration may contain conventional excipients such as the bonding agent, stuffing bulking agent, diluting agent, tablet compressing agent, lubricating agent, disintegrating agent, coloring agent, flavoring agent, and wetting agent. The suitable stuffing bulking agents include starch, sucrose, cellulose, mannitol, lactose, and other similar ones. The suitable disintegrating agents include starch, polyvinyl pyrrolidone and starch derivatives such as sodium starch glycolate. The suitable lubricating agents include, for example, magnesium stearate. The solid form of the compositions for oral administration can be prepared through conventional methods including mixing, filling, tablet compressing, et al. Repeated mixing allows the active pharmaceutical substance to be distributed throughout the compositions containing a large amount of stuffing bulking agent. The excipients commonly-used include mannitol, sorbitol, sodium pyrosulfite, sodium hydrogen sulfite, sodium thiosulfate, cysteine hydrochloride, thioglycolic acid, methionine, vitamin C, disodium EDTA, calcium disodium edetate, carbonates of alkali metal and aqueous solutions thereof, acetates of alkali metal and aqueous solutions thereof, phosphates of alkali metal and aqueous solutions thereof, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, silicon derivatives, cellulose and its derivatives, alginate, gelatin, polyvinyl pyrrolidone, glycerol, Tween 80, agar, calcium carbonate, calcium bicarbonate, surfactant, polyethylene glycol, cyclodextrin, β-cyclodextrin, phospholipids, kaolin, pulvis talci, calcium stearate, magnesium stearate, et al.

The usage and dosage of the pharmaceutical composition of the present invention are determined according to conditions of diseases while being used. For example, the pharmaceutical composition can be administered 1-6 times a day for 1-10 doses each, and each dose can be 0.1 mg-1000 mg.

The new use of FG provided by the present invention has the following advantages:

FG can significantly lower the levels of ALT and AST in serum, improve steatosis and lobular inflammation, reduce the degree of hepatocellular ballooning degeneration, and improve the pathological score of liver damage. The final results demonstrate that the present invention can be used to treat NASH with superior effectiveness to prior art.

DETAILED DESCRIPTION OF IMPLEMENTATION

The present invention will now be further demonstrated using the following embodiments.

For the preparation method of FG used in the present invention, see Embodiment 4 of CN103193878A, which is shown below.

Embodiment 1: Preparation of Water Injections

1. Composition: FG protein (concentration: 10 mg/mL), histidine (pharmaceutical grade, concentration: 10 mg/mL), citric acid-sodium citrate buffer (20 mM sodium citrate-citric acid, 100 mM NaCl, pH5.5±0.1).

2. Preparation Method 1) 12.5 mg/mL FG protein solution, the buffer system is citric acid-sodium citrate, and the pH is adjusted to 5.5±0.1, prepared for use;
2) 50 mg/mL histidine mother liquor, the buffer system is citric acid-sodium citrate, the pH is adjusted to pH 5.5±0.1, prepared for use;
3) Mix the FG protein solution of step 1) and the histidine mother liquor of step 2) according to the volume ratio of 4:1, and transfer 500 μL of the mixed solution into 2 mL penicillin bottles.

Experiment Example 1: Therapeutic Effect of FG in an Effective Dose Range in a Mouse Model of MCD (Methionine Choline Deficient) Diet-Induced NASH A mouse model of MCD diet-induced NASH is used in this experiment, mainly because this diet has been used for more than 40 years and its production process has become more mature. In addition, the characterization this diet induced has obtained multiple verification in terms of its rapidity (i.e. NASH related symptoms can be triggered in about 4 weeks) and effectiveness (i.e. symptoms induced have great similarity to those of human NASH).

1. Experimental Method

After adaptive feeding for two weeks, C57BL male mice of eight-week-old were began to be fed MCD diet. After MCD diet fed for two weeks, the mice were randomly divided into 4 groups according to the body weight: a solvent group, a FGF-21 group, a low-dose FG group, and a high-dose FG group. There were 10 mice in each group and they were administered once a day via hypodermic injection for two weeks.

Details of animal grouping and administration are shown in Table 1:

TABLE 1

| Animal grouping and administration | | | |
|---|---|---|---|
| Group | n | Dose | Administration period (day) |
| Solvent group | 10 | Solvent in the same volume | 14 d |
| FGF-21 group | 10 | 0.4 mg/kg/d | 14 d |
| Low-dose FG group | 10 | 0.125 mg/kg/d | 14 d |
| High-dose FG group | 10 | 2 mg/kg/d | 14 d |

After the administration, the mice were killed and their relevant tissues were removed for subsequent analyses.

2. Indices Detection 2.1 the Blood Serum was Separated and Various Biochemical Indices Therein were Detected: Levels of ALT and AST in Serum were Determined Using a Clinically General Assay Kit (Provided by Shanghai Shensuo-UNF Medical. Diagnostic Articles Co., Ltd).

2.2 Histomorphological Examination on Mouse Liver Tissue

Morphological changes in mouse liver were observed through H & E staining method. The specific steps were as follows: The freshly removed small piece of liver was fixed in formalin solution overnight, and embedded in paraffin after gradient dehydration, then sectioned into 5 μm slices. The liver sections were stained with hematoxylin-eosin, and finally the morphology of liver tissue of each mouse was observed under a microscope.

2.3 Detection of Collagen Fibers in Mouse Liver Tissue

The collagen deposition in mouse liver was observed through Sirius Red (SR) staining method. The specific steps were as follows: The liver sections from paraffin blocks were stained using the Sirius Red staining kit, and finally the fibrosis of liver tissue of each mouse was observed under a microscope.

There is a scoring system for assessing the severity of NASH in clinical practice, i.e., NASH Clinical Research Network Scores, mainly including three aspects: steatosis, lobular inflammation, and ballooning degeneration. In this experiment, five mice were randomly selected from each group, and five microscopic fields of view within the H & E stained liver tissue sections of the corresponding mouse were randomly selected based on which a score is given from the above three aspects, objectively evaluating the degree of hepatitis of mice in each group.

3. SPSS16.0 Statistical Software was Used for Statistics and Data Analysis. A t-Test was Used to Compare the Difference Between Two Groups of Data. One-Way ANOVA Test and Multiple Linear Regression Analysis were Used to Compare Differences Among Multiple Groups of Data. The Difference was Statistically Significant with P<0.05

4. Experimental Results 4.1 Effect of FG on Serum ALT Level as Shown in Table 2:

TABLE 2

Effect of FG on serum ALT level

| | Solvent group | FGF-21 group | Low-dose FG group | High-dose FG group |
|---|---|---|---|---|
| Serum ALT(U/L) | 199.8 ± 30.8 | 100.2 ± 20.6* | 51.1 ± 7.7*Δ | 39.9 ± 4.1*Δ |

(1) Data shown in the table represented the mean ± standard error;
(2) *compared with the solvent group P < 0.05;
***compared with the solvent group P < 0.001;
Δcompared with the FGF-21 group P < 0.05.

As shown in Table 2, after two weeks of treatment, the ALT level of mice with NASH in the FGF-21 group decreased to 100.2±20.6 U/L, and there was a significant difference compared with the solvent group with the ALT level 199.8±30.8 U/L (P<0.05). The levels of ALT in the low-dose FG group and high-dose FG group decreased to 51.1±7.7 U/L and 39.9±4.1 U/L, respectively, and a significant difference was found compared with the solvent group (P<0.001) as well as the FGF-21 group (P<0.05). These results indicate that FG not only has the efficacy of lowering ALT levels but also its efficacy herein is better than FGF-21.

4.2 Effect of FG on Serum AST Level as Shown in Table 3:

TABLE 3

Effect of FG on serum AST level

| | Solvent group | FGF-21 group | Low-dose FG group | High-dose FG group |
|---|---|---|---|---|
| Serum ALT(U/L) | 196.9 ± 29.3 | 115.7 ± 15.9* | 74.4 ± 7.9Δ | 73.7 ± 7.8Δ |

(1) Data shown in the table represented the mean ± standard error;
(2) *compared with the solvent group P < 0.05;
**compared with the solvent group P < 0.01;
Δcompared with the FGF-21 group P < 0.05.

As shown in Table 3, after two weeks of treatment, the AST level of mice with NASH in the FGF-21 group decreased to 115.7±15.9 U/L, and there was a significant difference compared with the solvent group with the AST level 196.9±29.3 U/L (P<0.05). The levels of AST in the low-dose FG group and high-dose FG group decreased to 74.4±7.9 U/L and 73.7±7.8 U/L, respectively, and a significant difference was found compared with the solvent group (P<0.01) as well as the FGF-21 group (P<0.05). These results indicate that FG not only has the efficacy of lowering ALT levels but also its efficacy herein is better than FGF-21.

4.3 Effect of Improvement on NASH Clinical Scores as Shown in Table 4:

TABLE 4

Effect of improvement on NASH clinical scores

| | Steatosis | Lobular inflammation | Ballooning | Total score |
|---|---|---|---|---|
| Solvent group | 2.2 ± 0.2 | 2.6 ± 0.1 | 1.3 ± 0.1 | 6.0 ± 0.21 |
| FGF-21 group | 2.0 ± 0.3 | 2.1 ± 0.2 | 0.9 ± 0.1** | 4.7 ± 0.5* |
| Low-dose FG group | 1.8 ± 0.3 | 0.7 ± 0.1*ΔΔΔ | 0.7 ± 0.1 | 3.2 ± 0.4***Δ |
| High-dose FG group | 0.9 ± 0.3Δ | 0.6 ± 0.2*ΔΔΔ | 0.4 ± 0.1*ΔΔ | 1.9 ± 0.5*ΔΔ |

(1) Data shown in the table represented the mean ± standard error;
(2) *compared with the solvent group $P < 0.05$;
**compared with the solvent group $P < 0.01$;
***compared with the solvent group $P < 0.001$;
Δcompared with the FGF-21 group $P < 0.05$;
ΔΔcompared with the FGF-21 group $P < 0.01$;
ΔΔΔcompared with the FGF-21 group $P < 0.001$.

As shown in Table 4, after two weeks of treatment, both the scores for ballooning and NASH total scores in FGF-21 group had improved significantly ($P<0.05$) compared with the solvent group, whereas no significant improvement in scores for lobular inflammation had been observed ($P>0.05$). Compared with the solvent group, there was a significant improvement in both low-dose FG group and high-dose FG group in terms of scores for lobular inflammation, scores for ballooning and NASH total scores. Scores for steatosis in high-dose FG group had been significantly improved compared with the solvent group. In addition, in comparison with FGF-21 group, all scores for steatosis, lobular inflammation, ballooning and the total thereof had been significantly improved in low-dose FG group and/or high-dose FG group. These results indicate that FG not only has the efficacy of improving lobular inflammation, ballooning, and NASH total scores but also its efficacy herein is better than FGF-21.

5. Experimental Results

Detections after injection of FG show that compared with the solvent group and FGF-21 group, low-dose FG group and/or high-dose FG group can significantly lower the levels of ALT and AST in serum, improve steatosis and lobular inflammation, reduce the degree of hepatocellular ballooning degeneration, and improve the pathological score of liver damage. These results indicate that FG has the effect of treating NASH.

6. Conclusion: FG has the Clinical Application Value in the Treatment of NASH which is Superior to the Prior Art The protein of the instant disclosure (SEQ ID NO: 1) is modified with polyethylene glycol (also called PEGylation). Polyethylene glycol modification is chemically conjugated to via the activated polyethylene glycol to proteins, peptides, small molecular organic drugs and liposomes, thereby increasing the stability of the medicinal effective protein, prolonging its half-life in vivo, and reducing immunogenicity.

The conjugate may be prepared by a method in the presence of sodium cyanoborohydride, the protein reacts with mPEGALD to obtain the conjugate. In the reaction: the mass ratio of the protein to mPEG-ALD can be 1:4, the reaction can be carried out in a citric acid buffer at pH 6.0. At the beginning of the reaction, the concentration of the protein can be 2.0 mg/ml. At the beginning of the reaction, the amount of sodium cyanoborohydride added can be 10 times the number of moles of mPEG-ALD. The temperature of the reaction can be 4° C., and the reaction time can be 8 hours. The molecular weight of the mPEG-ALD is 5 kD to 80 kD, specifically 20 kD-40 kD. The method can also include the following purification steps: taking the reaction solution containing the conjugate, desalting with Sephadex G25 and replacing the PEG-mFGF-21 mature peptide with a desalting buffer (pH 8.0, 20 mM Tris-HCl buffer solution), and then performing Capto Q anion exchange chromatography. The specific parameters of Capto Q anion exchange chromatography is: XK16/26 Column, the column height is 10 cm, filled with GE Capto Q anion exchange resin; the eluent is Solution A, Solution B or a mixture of Solution A and Solution B, Solution A is pH 8.0, 20 mM Tris-HCl buffer solution, Solution B is pH8.0, 20 mM Tris-HCl buffer solution containing 1 M NaCl; elution process, 0-20 min, the volume ratio of Solution B in the eluate rising linearly from 0% to 100%, the flow rate is 10 mL/min, and collecting the post-column solution with conductivity between 3 ms/cm and 20 ms/cm, thus obtaining the PEG-mFGF-21 mature peptide solution.

Embodiment 4 of CN103193878 Preparation of polyethylene glycol-modified mFGF-21 mature peptide (PEG-mFGF-21 mature peptide)

I. Preparation of PEG-mFGF-21 Mature Peptide

Taking the mFGF-21 mature peptide solution, desalting with Sephadex G25 and replacing the mFGF-21 mature peptide with citric acid buffer (the solvent is water, the solute and its concentration are as follows: 20 mM sodium citrate, 80 mM sodium Chloride; pH 6.0), using hollow fiber column ultrafiltration to concentrate to a protein concentration of 2.0 mg/ml, adding mPEG-ALD to make the mass ratio of mFGF-21 mature peptide to mPEG-ALD at 1:4, adding sodium cyanoborohydride to make it 10 times the mole number of mPEG-ALD, reacting at 4° C. for 8 h, and adding glycine to terminate the reaction.

II. Purification of PEG-mFGF-21 Mature Peptide

Taking the reaction solution obtained in Step I, desalting with Sephadex G25 and replacing the PEG-mFGF-21 mature peptide with desalting buffer (pH8.0, 20 mM Tris-HCl buffer), and then performing Capto Q anion exchange chromatography. The specific parameters of Capto Q anion exchange chromatography: XK16/26 Column, column height 10 cm, filled with GE Capto Q anion exchange resin; eluent is Solution A, Solution B or a mixture of Solution A and Solution B, Solution A is pH 8.0, 20 mM Tris-HCl buffer solution, Solution B is pH 8.0, 20 mM Tris-HCl buffer solution containing 1 M NaCl; elution process, 0-20 min, The volume ratio of liquid B in eluent increased linearly from 0% to 100%, the flow rate is 10 mL/min, and the solution passed the column with conductivity between 3 ms/cm and 20 ms/cm was collected, thus obtaining the PEG-mFGF-21 mature peptide solution.

Embodiment 5 of CN103193878 Physicochemical Properties of PEG-mFGF-21 Mature Peptide I. Determination of Molecular Weight and Purity The molecular weight and purity of the PEG-mFGF-21 mature peptide and the mFGF-21 mature peptide prepared were determined by SDS PAGE electrophoresis and HPLC high performance liquid chromatography, respectively.

SDS-PAGE: the concentrated gel concentration is 5%, the concentration of the separation gel is 15%, and staining with Coomassie Brilliant Blue R-250.

HPLC high performance liquid chromatography: the model of the analytical column is Biosuit250, 5 μm HR SEC, the mobile phase is pH 7.0, 0.2 mol/L phosphate buffer, the detection wavelength is 280 nm, with a flow rate of 0.5 mL/min.

Using SDS-PAGE, the molecular weights of mFGF-21 mature peptide and PEG-mFGF-21 mature peptide were determined to be about 25 kD and 55 kD, respectively. The results of HPLC high performance liquid chromatography show that the mature peptide of mFGF-21 appeared a high purity peak at 16.5 min, while the mature peptide of PEG-mFGF-21 appeared earlier due to the increase in molecular weight, and a peak with high purity appeared at 12 min. The purity of mFGF-21 mature peptide and PEG-mFGF-21 mature peptide can be more than 95%.

II. Determination of Temperature Stability

The temperature stability of the PEG-mFGF-21 mature peptide and the mFGF-21 mature peptide prepared were tested separately.

The method is as follows: Placing the test sample at room temperature for 1 month, and the sample stored at −80° C. was used as Control A, and the newly prepared sample was used as Control B, performing 15% SDS-PAGE analysis and cell viability determination respectively.

The results of SDS-PAGE show that the degradation rate of the mFGF-21 mature peptide is about 42% after being placed at room temperature for 1 month, while the PEG-mFGF-21 mature peptide has no obvious degradation after being placed at room temperature for one month. The activity retention rate of mFGF-21 mature peptide is about 27% after being stored at room temperature for 1 month, while the cell activity retention rate of PEG-mFGF-21 mature peptide is about 80% after being stored at room temperature for 1 month.

The above results indicate that the temperature stability of mFGF-21 mature peptide is significantly increased after PEG modification.

What is claimed is:

1. A method of treating non-alcoholic steatohepatitis (NASH), comprising administering a pharmaceutical composition comprising mPEG-CH$_2$—N$^\alpha$H-mFGF21 or a pharmaceutically acceptable salt thereof as a water injection to a subject having NASH in an amount of 0.125 mg/kg/day or 2 mg/kg/day, wherein mFGF21 consists of SEQ ID NO: 1, and wherein the method improves lobular inflammation.

2. The method according to claim 1 wherein the non-alcoholic steatohepatitis (NASH) is selected from the group consisting of hepatitis-induced NASH, obesity-induced NASH, diabetes-induced NASH, insulin resistance-induced NASH, hypertriglyceridemia-induced NASH, abetalipoproteinemia-induced NASH, NASH induced by glycogen storage disease, NASH induced by Wake's Disease, NASH induced by Wolman's disease, and lipodystrophia-induced NASH.

3. The method according to claim 1 wherein the pharmaceutical composition essentially consists of mPEG-CH$_2$—N$^\alpha$H-mFGF21 or a pharmaceutically acceptable salt thereof as the active pharmaceutical ingredient.

4. A method of treating non-alcoholic steatohepatitis (NASH), comprising administering a pharmaceutical composition comprising mPEG-CH$_2$—N$^\alpha$H-mFGF21 or a pharmaceutically acceptable salt thereof as a water injection to a subject in need thereof in an amount of 0.125 mg/kg/day or 2 mg/kg/day, wherein mFGF21 consists of SEQ ID NO: 1, wherein the method lowers levels of alanine aminotransferase or levels of aspartate aminotransferase in serum.

5. The method according to claim 4, wherein the method improves steatosis, lobular inflammation, or both.

6. The method according to claim 4 wherein the pharmaceutical composition essentially consists of mPEG-CH$_2$—N$^\alpha$H-mFGF21 or a pharmaceutically acceptable salt thereof as the active pharmaceutical ingredient.

7. A method of treating non-alcoholic steatohepatitis (NASH), comprising administering a pharmaceutical composition comprising mPEG-CH$_2$—N$^\alpha$H-mFGF21 or a pharmaceutically acceptable salt thereof as a water injection to a subject in need thereof in an amount of 0.125 mg/kg/day or 2 mg/kg/day, wherein mFGF21 consists of SEQ ID NO: 1, wherein the method improves steatosis, lobular inflammation, ballooning, or any combination thereof.

8. The method according to claim 7 wherein the pharmaceutical composition essentially consists of mPEG-CH$_2$—N$^\alpha$H-mFGF21 or a pharmaceutically acceptable salt thereof as the active pharmaceutical ingredient.

* * * * *

SEQUENCE LISTING

```
<160> NUMBER OF SEQ ID NOS: 1

<210> SEQ ID NO 1
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Tyr Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu Arg Leu Pro Gln Lys Asp Ser Pro Asn Gln Asp
        115                 120                 125

Ala Thr Ser Trp Gly Pro Val Arg Phe Leu Pro Met Pro Gly Leu Leu
    130                 135                 140
```

```
His Glu Pro Gln Asp Gln Ala Gly Phe Leu Pro Pro Glu Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Thr Ser
            180
```